United States Patent
Kao et al.

(10) Patent No.: US 9,182,340 B2
(45) Date of Patent: Nov. 10, 2015

(54) OPTICAL MEASURING APPARATUS AND OPTICAL MEASURING METHOD

(71) Applicant: LITE-ON IT CORPORATION, Taipei (TW)

(72) Inventors: Yu-Jin Kao, Hsinchu (TW); Yi-Kai Cheng, Hsinchu (TW); Shih-Chang Wang, Hsinchu (TW); Ta-Hsiang Wang, Hsinchu (TW); Timothy Liu, Hsinchu (TW)

(73) Assignee: Lite-On Technology Corporation, Taipei (TW)

( * ) Notice: Subject to any disclaimer, the term of this patent is extended or adjusted under 35 U.S.C. 154(b) by 90 days.

(21) Appl. No.: 13/859,759

(22) Filed: Apr. 10, 2013

(65) Prior Publication Data

US 2014/0118743 A1    May 1, 2014

(30) Foreign Application Priority Data

Oct. 31, 2012  (CN) .......................... 2012 1 0427897

(51) Int. Cl.
*G01N 21/00* (2006.01)
*G01N 21/25* (2006.01)

(52) U.S. Cl.
CPC ...... *G01N 21/253* (2013.01); *G01N 2201/0415* (2013.01); *G01N 2201/0626* (2013.01); *G01N 2201/0633* (2013.01)

(58) Field of Classification Search
CPC ........ G01N 35/00; G01N 21/59; G01N 21/25
USPC ........................................... 356/432, 435, 418
See application file for complete search history.

(56) References Cited

U.S. PATENT DOCUMENTS

| | | | |
|---|---|---|---|
| 4,477,190 A * | 10/1984 | Liston et al. | 356/418 |
| 5,508,200 A * | 4/1996 | Tiffany et al. | 436/44 |
| 6,429,936 B1 * | 8/2002 | Scaduto | 356/417 |
| 6,497,488 B1 * | 12/2002 | Yamauchi | G02F 1/133526 348/E9.027 |
| 7,692,794 B2 * | 4/2010 | Kim et al. | 356/418 |
| 8,823,940 B2 * | 9/2014 | Yeo | 356/435 |
| 2007/0077605 A1 * | 4/2007 | Hurt et al. | 435/7.21 |
| 2008/0137074 A1 * | 6/2008 | Furman | G01N 21/21 356/73 |
| 2009/0180120 A1 * | 7/2009 | Kanayama | 356/440 |

* cited by examiner

*Primary Examiner* — Tarifur Chowdhury
*Assistant Examiner* — Isiaka Akanbi
(74) *Attorney, Agent, or Firm* — Jianq Chyun IP Office

(57) ABSTRACT

An optical measuring apparatus comprising at least one light emitting unit, a stage, at least one lens, and at least one light detector is provided. The light emitting unit emits a light beam. The stage contains accommodating spaces. The accommodating spaces move to the transmission path of the light beam in turn. The lens is located between the light emitting unit and the stage, whose orthogonal projection on the stage appears substantially to be a polygon. When one of the accommodating spaces moves to the transmission path of the light beam, a perpendicular bisector half line of each side of the polygon is not overlapped with another adjacent accommodating space of the accommodating spaces. An optical measuring method is also provided.

21 Claims, 7 Drawing Sheets

OPTICAL MEASURING APPARATUS AND OPTICAL MEASURING METHOD

CROSS-REFERENCE TO RELATED APPLICATION

This application claims the priority benefit of China application serial no. 201210427897.7, filed on Oct. 31, 2012. The entirety of the above-mentioned patent application is hereby incorporated by reference herein and made a part of this specification.

TECHNICAL FIELD

The invention relates to an optical measuring apparatus and an optical measuring method.

BACKGROUND

In biomedical applications, optical detection techniques are often relied on to measure micro samples, such as absorption states of red blood cells etc., to a particular light, in order to respond the content or the composition ratio of specific substances within the cells. Generally speaking, the conventional optical detection techniques usually use laser light as a light source. However, the size and power consumption of the laser light source is large, and its price is relatively high, which makes the optical measuring apparatus expensive. In contrast, light emitting diodes (LEDs) are relatively small, cheap, low power consumption, and low heat generation, as the semiconductor technology has been progressively developed in recent years. As a result, the light emitting diodes have gradually replaced the laser light source to be the light source for certain biomedical detection apparatus.

However, the light shape and intensity distribution of a common light emitting diode are not uniform, which could cause difficulties in optical alignment for the measurement within a micro-volume sample. This may significantly affect the accuracy and resolution of the optical detection, and thus limit the application of light emitting diodes optical detection for biomedical applications. In some cases, when a plurality of light emitting diodes are used in an optical measurement apparatus, a plurality of light beams emitted from the light emitting diodes may generate light-signal interferences between each other. Such interference normally increases the measurement noise, causes skewed optical signal, and may result in misjudgment of the sample conditions. Thus apparatus and methods to overcome such limitations of LEDs in biomedical measurement devices are needed.

SUMMARY

Accordingly, the invention is directed to an optical measuring apparatus adapted to measure a plurality of different properties of a plurality of samples.

The invention is directed to an optical measuring method adapted to measure a plurality of samples.

One of the embodiments in the invention provides an optical measuring apparatus adapted to measure at least one sample. The optical measuring apparatus includes at least one light emitting unit, a stage, at least one lens and at least one light detector. The light emitting unit is configured to emit a light beam. The stage is disposed in a transmission path of the light beam, and includes a plurality of accommodating spaces, wherein the accommodating spaces accommodate the sample respectively, and the accommodating spaces move to the transmission path of the light beam in turn. The lens is disposed in the transmission path of the light beam and is located between the light emitting unit and the stage, and an orthogonal projection of the lens on the stage substantially appears to be a polygon, wherein when one of the accommodating spaces moves to the transmission path of the light beam, a perpendicular bisector half line of each side of the polygon is not overlapped with another adjacent accommodating space of the accommodating spaces, wherein the perpendicular bisector half line is the line starting from the midpoint of the side of the polygon and perpendicularly extending away from the side of the polygon. The light detector is disposed in the transmission path of the light beam going through the stage, so as to detect the light beam.

According to an embodiment of the invention, the at least one lens includes a plurality of lenses, the at least one light emitting unit includes a plurality of light emitting units and the at least one light detector includes a plurality of light detectors, wherein the light beams emitted from the light emitting units are respectively transmitted to the stage through the lenses and are respectively transmitted to the light detectors, and the stage is rotated in order for the accommodating spaces to move to the transmission paths of the light beams in turn where the light beams emitted from the light emitting units are respectively a plurality of light beams with different properties.

According to an embodiment of the invention, the optical measuring apparatus further includes a control unit electrically connected to the light emitting units and the light detectors, and the control unit drives the light emitting units to emit the light beams in turn, wherein when any one of the light emitting units emits the light beam, the accommodating spaces move to the transmission path of the light beam in turn, the light detectors convert the measured light beams into a plurality of electric signals for transmitting to the control unit, and the control unit analyzes the electric signals.

According to an embodiment of the invention, the optical measuring apparatus further includes an actuator connected to the stage so as to drive the stage to rotate, and the control unit is electrically connected to the actuator and synchronizes the duration of light-emitting of the light emitting units and the rotating time of the stage to cooperate with each other.

According to an embodiment of the invention, the optical measuring apparatus further includes a control unit electrically connected to the light emitting units and the light detectors, and the control unit drives the light emitting units to emit the light beams at the same time, wherein the accommodating spaces move to the transmission paths of the light beams in turn, the light detectors convert the measured light beams into a plurality of electric signals for transmitting to the control unit, and the control unit analyzes the electric signals.

According to an embodiment of the invention, the stage rotates continuously when the light detector detects the light beam.

According to an embodiment of the invention, wavelength ranges of the light beams are different from each other.

According to an embodiment of the invention, the lens has a light incident surface, a light emitting surface opposite to the light incident surface and a plurality of side surfaces connected to the light incident surface and the light emitting surface, wherein the light beam emitted from the light emitting unit passes through the light incident surface and the light emitting surface sequentially, and the orthogonal projections of the side surfaces form the plurality of sides of the polygon on the stage respectively.

According to an embodiment of the invention, the light incident surface is a flat surface and the light emitting surface is a curved surface protruded away from the light incident surface.

According to an embodiment of the invention, the light incident surface is a curved surface protruded towards the light emitting unit, and the light emitting surface is a curved surface protruded away from the light incident surface.

According to an embodiment of the invention, the light incident surface has a plurality of optical micro structures.

According to an embodiment of the invention, each of the light incident surfaces of at least a portion of the lenses has a plurality of optical micro structures, and the optical micro structures belonging to the different lenses are identical to each other or at least partially different from each other.

According to an embodiment of the invention, the optical measuring apparatus further includes a filter unit disposed in the transmission path of the light beam and located between the light emitting unit and the light detector.

According to an embodiment of the invention, the optical measuring apparatus further includes a temperature control unit to maintain a temperature of the sample within a predetermined temperature range.

One of the embodiments in the invention provides an optical measuring apparatus adapted to measure at least one sample. The optical measuring apparatus includes a plurality of light emitting units, a stage and a plurality of light detectors. The light emitting units emit a plurality of light beams with different properties in turn. The stage is disposed in the transmission paths of the light beams, and includes a plurality of accommodating spaces, wherein the accommodating spaces accommodate the sample respectively, wherein when any one of the light emitting units emits one of the light beams, the accommodating spaces move through the transmission path of the light beam in turn. The light detectors are respectively disposed in the transmission paths of the light beams passing through the stage so as to detect the light beams.

According to an embodiment of the invention, the optical measuring apparatus further includes a plurality of lenses disposed between the light emitting units and the stage, wherein each of the lenses has a light incident surface, a light emitting surface opposite to the light incident surface and a plurality of side surfaces connected to the light incident surface and the light emitting surface, and the light beam emitted from each of the light emitting units passes through the light incident surface and the light emitting surface sequentially, and an orthogonal projection of each of the lenses on the stage substantially appears to be a polygon.

One of the embodiments of the invention provides an optical measuring method adapted to measure a plurality of samples, and the optical measuring method includes: providing a plurality of light beams with different properties in turn; when any one of the light beams is provided, moving the samples, in turn, across the transmission path of the provided light beam; and converting the light beam, through which the samples are moved across, into an electric signal.

According to an embodiment of the invention, the light beams with different properties are provided in a specific sequence, and the specific sequence is repeated until the analysis is finished.

According to an embodiment of the invention, the method for moving the samples to the transmission path of the light beam in turn includes rotating the samples around a rotation center in order for the samples to move across the transmission path of the light beam in turn.

According to an embodiment of the invention, the optical measuring method further includes: amplifying the electric signals converted respectively from the light beams; and analyzing the amplified electric signals so as to determine the properties of the samples respectively.

According to an embodiment of the invention, the optical measuring method further includes: analyzing the electric signals converted from the light beams in turn, wherein when any one of the light beams is provided, the electric signal converted from the light beam is analyzed.

According to an embodiment of the invention, the optical measuring method further includes: applying a plurality of lenses to limit irradiation ranges of the light beams respectively, wherein when one of the samples moves to the transmission path of any one of the light beams, another adjacent sample of the said samples is located outside the irradiation range of the light beam.

According to an embodiment of the invention, the samples include a biological sample or a non-biological sample.

According to an embodiment of the invention, the samples are a plurality of identical samples.

In light of the above, the optical measuring apparatus of the embodiments of the invention may reduce the interferences between the lights of the light emitting units on the samples located at the accommodating spaces on the stage through the lenses disposed in the light emitting units. The optical measuring apparatus in the embodiments of the invention may detect the different properties of the samples, by moving the accommodating spaces in turn to the transmission paths of the light beams with different properties that emitted from the light emitting units with different properties. In addition, the optical measuring method in the embodiments of the invention may measure the properties of the samples and reduce the interferences between the light beams of different properties, by providing the light beams with different properties in turn and moving the samples to the transmission path of the light beam when any one of the light beams is provided.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
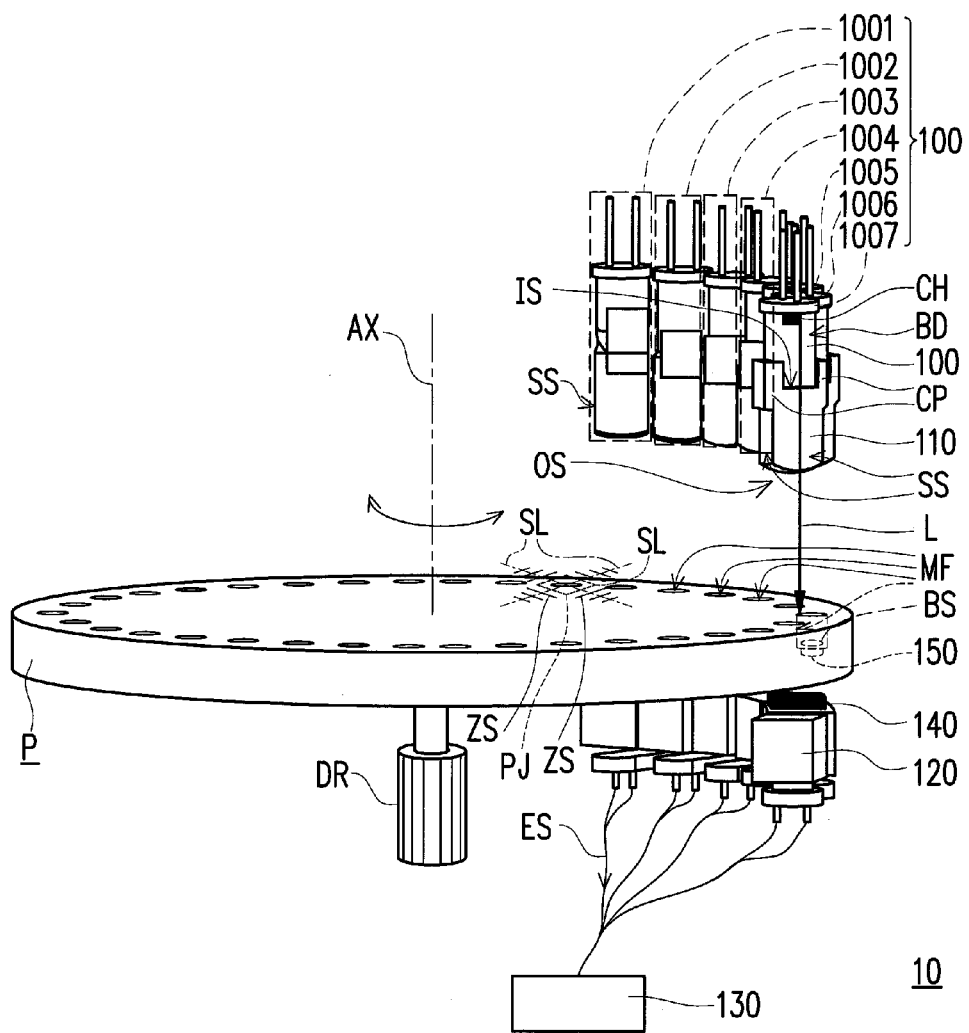
FIG. 1A is a schematic diagram of an optical measuring apparatus according to an embodiment of the invention.

Reference will now be made in detail to the present embodiments of the invention, examples of which are illustrated in the accompanying drawings. Wherever possible, the same reference numbers are used in the drawings and the description to refer to the same or like parts.

FIG. 1A is a schematic diagram of an optical measuring apparatus according to an embodiment of the invention. Referring to FIG. 1A, in the embodiment, the optical measuring apparatus 10 is adapted to measure at least one sample BS, wherein the sample BS may include a biological sample or a non-biological sample. In the embodiment, the quantity of the samples BS is, for example, more than one. However, the invention is not limited thereto. Moreover, the samples BS may also be a plurality of identical samples BS or individually different samples BS, but the invention is also not limited thereto. The optical measuring apparatus 10 includes at least one light emitting unit 100, a stage P, at least one lens 110 and at least one light detector 120. The light emitting unit 100 is configured to emit a light beam L. In the embodiment, the quantity of the light emitting units 100 is, for example, 7, but the invention is not limited thereto. The stage P is disposed on a transmission path of the light beam L, and includes a plurality of accommodating spaces MF, wherein the accommodating spaces MF accommodate the sample BS respectively, and the accommodating spaces MF move to the transmission path of the light beam L in turn. The lens 110 is disposed in the transmission path of the light beam L, and is located between the light emitting unit 100 and the stage P. An orthogonal projection of the lens 110 on the stage P appears substantially to be an orthogonal projection PJ of a polygon, as a tetragon illustrated in FIG. 1B. In addition, the light detector 120 is disposed in the transmission path of the light beam L passing through the stage P, so as to detect the light beam L, wherein the samples BS are biological samples such as blood, cells or tissue slices etc. In other embodiments, the samples BS may also be chemical samples, which may include organic aromatic hydrocarbons, and the organic aromatic hydrocarbons may include at least one of benzene, naphthalene, anthracence and other compounds, but the invention is not limited thereto. The light beam L may carry an optical signal of the sample BS after irradiating the sample BS, and the light detector 120 may receive the optical signal in order to be subsequently analyzed. In the embodiment, the light detector 120 is, for example, a photodiode (PD), but the invention is not limited thereto. In other embodiments, the light detector 120 may also be a photo-multiplier tube (PMT), a charge-coupled device (CCD) or other appropriate photoelectrical elements. Moreover, a material of the accommodating spaces MF in the embodiment is preferably a material having high transmittance and low bio-reactivity, such as polymethyl methacrylate (PMMA), polydimethyl siloxane (PDMS) or polycarbonate (PC). However, the invention is not limited thereto.

Figure 1B:
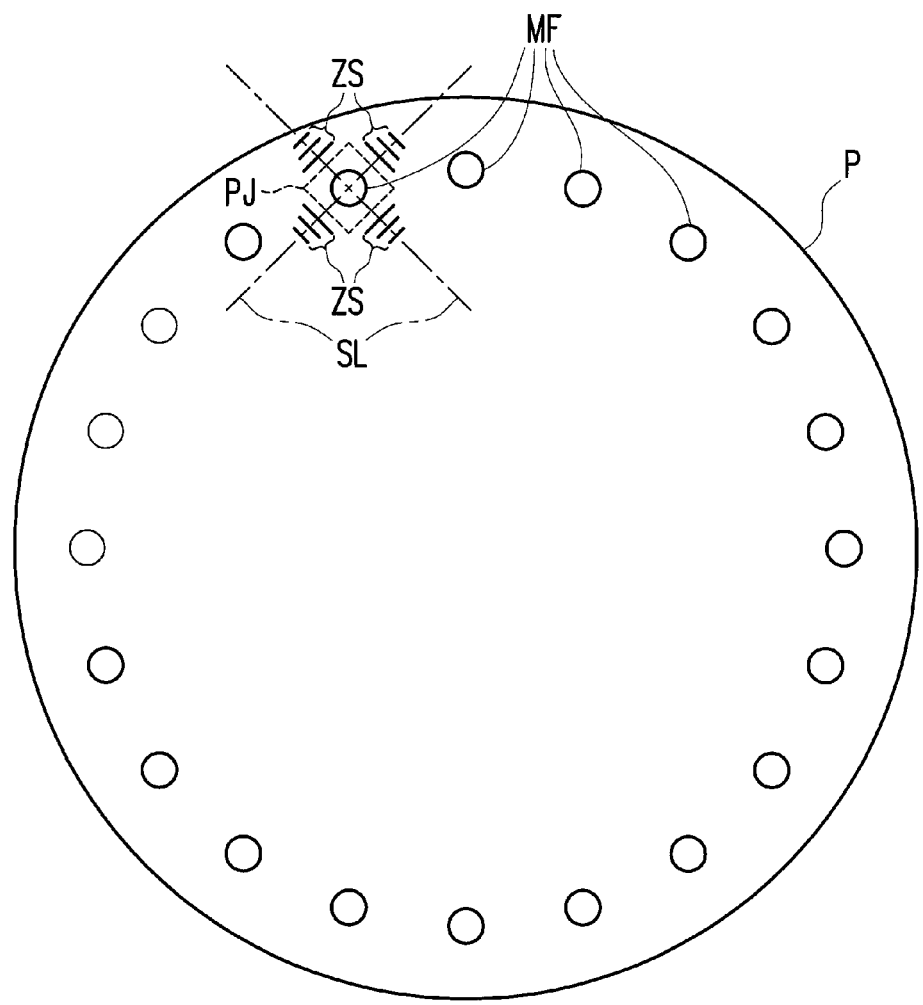
FIG. 1B is a top view of a stage of the optical measuring apparatus depicted in FIG. 1A.

FIG. 1B is a top view of a stage of the optical measuring apparatus depicted in FIG. 1A. Referring to FIG. 1A and FIG. 1B, in the embodiment, the lens 110 is capable of changing shapes of emitted lights of the light emitting units 100, thereby decreasing the interference phenomenon caused by measuring the light emitting units 100. More specifically, when one of the accommodating spaces MF moves to the transmission path of the light beam L, a perpendicular bisector half line SL of each side of the orthogonal projection of the lens 110 on the stage P (that is, the orthogonal projection PJ of the polygon) is not overlapped with another adjacent accommodating space MF, wherein the perpendicular bisector half line SL is the line starting from the midpoint of the side of the orthogonal projection PJ of the polygon and extending along the perpendicular bisector half line of the side away from the orthogonal projection PJ of the polygon. For example, the lens 110 in FIG. 1A is the lens having a quadrangle prism shape, and the orthogonal projection PJ of the lens 110 on the stage P is the tetragon such as a square. In the embodiment depicted in FIG. 1A, the light shape of the light beam L emitted from the light emitting unit 100 may change after passing through the lens 110, and the light intensity distribution thereof is concentrated within the orthogonal projection PJ, however, there might be light fringes ZS distributed on the directions along the perpendicular bisector half lines SL of the four sides of the orthogonal projection PJ, as illustrated in FIG. 1B. If the light fringes ZS overlap with the adjacent accommodating space MF and irradiated to the sample BS located in the adjacent accommodating space MF, interference may occur wherein the measured results may be affected. Moreover, in other examples, if the lens 110 is a cylindrical lens, the light spot thereof may spread outwards in all directions from the center of the orthogonal projection PJ of the cylindrical lens on the stage P, and its radiation might interfere with the adjacent accommodating space MF. In the embodiment of FIG. 1A, the light fringes ZS on the directions along the perpendicular bisector half lines SL of the four sides of the orthogonal projection PJ does not overlap with the adjacent accommodating spaces MF, through adjusting the disposition location and angle of the lens 110, the aforementioned interference can be prevented, resulting in enhanced reliability of the measurements.

Figure 2A:
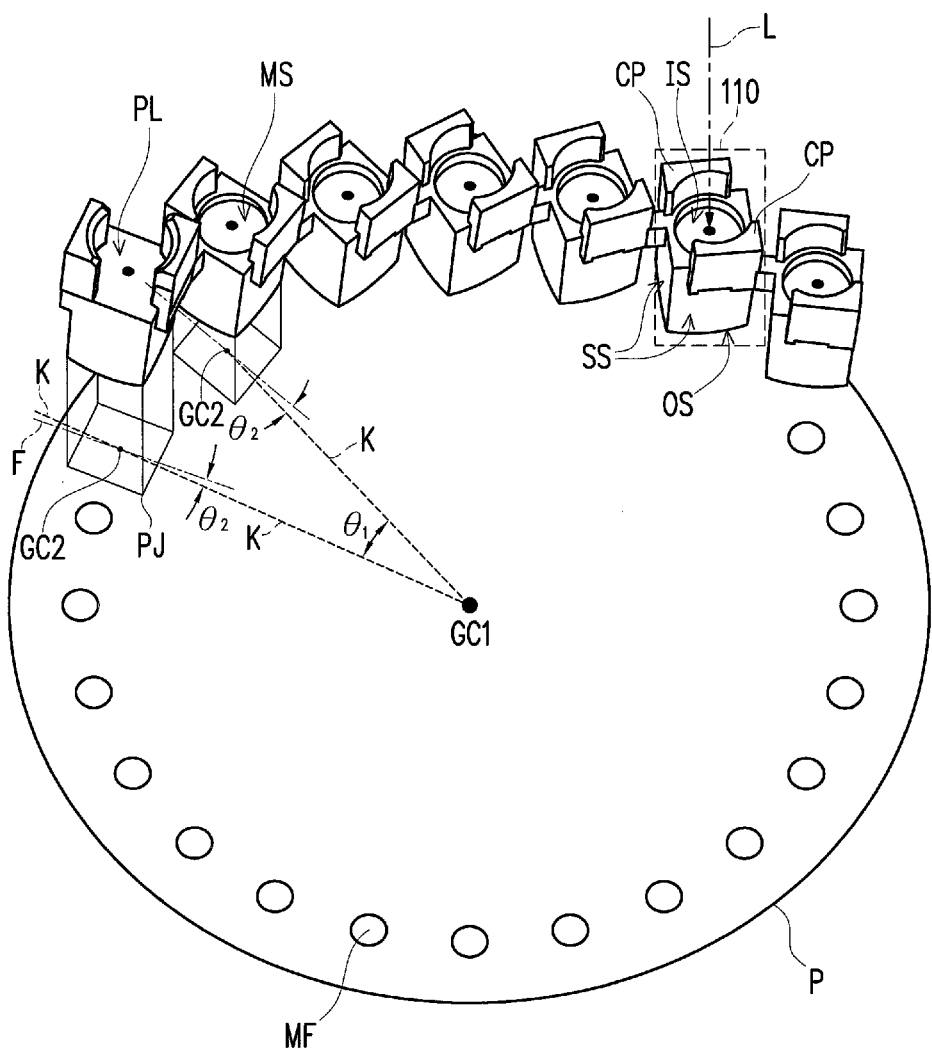
FIG. 2A is a schematic diagram of an arrangement of the lenses depicted in FIG. 1A.
Figure 2B:
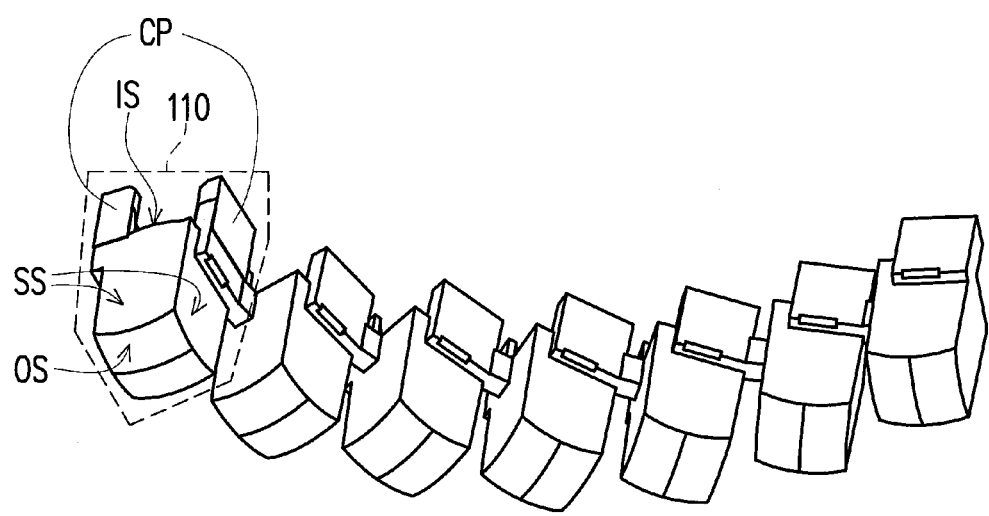
FIG. 2B is a schematic diagram of another perspective view of the arrangement of the lenses depicted in FIG. 2A.

FIG. 2A is a schematic diagram of an arrangement of the lenses depicted in FIG. 1A, and FIG. 2B is a schematic diagram of another perspective view of the arrangement of the lenses depicted in FIG. 2A. Referring to FIG. 1A through FIG. 2B, to be specific, the lenses 110 may be integrally formed by injection molding or may comprise a plurality of individual lenses 110. The stage P may rotate around a rotation center GC1. In the embodiment, the configuration of the lenses 110 should satisfy the following equations:

$$\frac{(N-2) \cdot 180°}{2N} \geq \theta_2 \geq \frac{(N-2) \cdot 180°}{2N} - \theta_1, \text{ and}$$

$$\frac{(N-2) \cdot 180°}{2N} > \theta_1 > 0$$

where $\theta_1$ is the angle between the two lines K and K' that are defined by the rotation center GC1 and the two geometric centers GC2 of two neighbouring orthogonal projections PJ of the polygons (such as the orthogonal projections PJ of the squares illustrated in FIG. 1A and FIG. 2A), corresponding to any two adjacent lenses 110; $\theta_2$ is the minimal angle between the connecting line K from the rotation center GC1 to the geometric center GC2 of the orthogonal projection PJ of the polygon and a normal line F of the sides of the orthogonal projection PJ of the polygon (such as the orthogonal projections PJ of the squares illustrated in FIG. 1A and FIG. 2A) of any one of the lenses 110; and N is the number of sides of the orthogonal projection PJ of the polygon. In the illustrated embodiment, N=4, that is, the orthogonal projection PJ of the polygon is a square, but the invention is not limited thereto. In addition, in the embedment, $\theta_2$ of the different lenses 110 may be equal to each other or at least partially different from each other, and $\theta_1$ of these lenses 110 may be equal to each other or at least partially different from each other. Therefore, the plurality of lenses 110 may prevent the light fringes ZS to interfere with the samples BS in the adjacent accommodating spaces MF through the aforementioned arrangement, in order to ensure the accuracy and reliability of the measurements.

More specifically, referring to FIG. 1A through FIG. 2B, the stage P may rotate in order for the accommodating spaces MF to move across the transmission paths of the light beams L in turn, and the light beams L emitted from the light emitting units 100 are respectively a plurality of light beams with different properties. For example, the light beams L emitted from the light emitting units 100 in the embodiment may be visible light or invisible light. In detail, the user may select a light emitting unit 100 capable of emitting an appropriate wavelength according to the sample and properties to be determined. For example, when the value to be determined is the concentration of blood oxygen saturation in human blood, the light emitting unit 100 may be the light emitting diode that emits near-infrared light and red light. Alternatively, when the value to be determined is the fluorescence intensity of biological tissues, the light emitting unit 100 may also be the light emitting diode that emits blue light. However, the invention is not limited thereto.

Referring to FIG. 1A through FIG. 2B again, in further detail, the optical measuring apparatus 10 may further include a control unit 130 that is electrically connected to the light emitting units 100 and the light detectors 120. The optical measuring apparatus 10 may further include an actuator that is connected to the stage P so as to drive the stage P to rotate along a rotation axis AX, wherein the stage P may rotate continuously when the light detector 120 detects the light beams L. Moreover, the control unit 130 is electrically connected to the actuator DR and causes light-emitting times of the light emitting units 100 and the rotating time of the stage P to cooperate with each other, wherein the control unit 130 may drive the light emitting units 100 to emit the different light beams L in turn. When any one of the light emitting units 100 emits the light beam L, the accommodating spaces MF move to the transmission path of the light beam L in turn, then the light detectors 120 convert the measured light beams L into a plurality of electric signals ES for transmitting to the control unit 130, and the control unit 130 analyzes the electric signals ES so as to measure the properties of the samples BS. In one embodiment, the control unit 130 may drive a single light emitting unit 1002 to emit light, here the stage P may rotate continuously in order for all the accommodating spaces MF on the stage P to be irradiated by the light emitting unit 1002 and for the light detectors 120 to receive the optical signals belonging to the samples BS in the accommodating spaces MF. After the signal receiving is completed, the control unit 130 may turn off the light emitting unit 1002 and drive another light emitting unit 1003 to emit and obtain the signals of the samples BS in the same manner. In another embodiment, the control unit 130 may drive all the light emitting units 100 to irradiate these optical samples BS in turn. The wavelength ranges of the light emitting units 100 in the embodiment may be different from each other (for example, the wavelength range thereof may be from 340 nm to 940 nm), such that the wavelength range may be configured to detect the different properties in each type of the samples BS rapidly. It should be noted that, the control unit 130 is to drive each individual light emitting unit of the light emitting units 100 in turn, one at a time. Therefore, the interference between the different light sources may be prevented when the measurement is taken and the measured results may be free from being affected by any other light source, and the properties of the samples BS may also be rapidly detected, so as to enhance the reliability and efficiency of the measurements.

Alternatively, the control unit 130 in the embodiment of FIG. 1A may also drive the light emitting units 100 to substantially emit more than one light beams at the same time, and move the accommodating spaces MF in turn to the transmission paths of the said light beams L. The lenses 110 corresponding to the light emitting units 100 can prevent the light fringes ZS that are generated by the light beams L passing through the lenses 110 to irradiate the samples BS in the adjacent accommodating spaces MF through the arrangement in FIG. 2A, so that the interference arising from the light fringes ZS can be minimized. Therefore, the properties of the samples BS can be rapidly detected, further enhancing the reliability and efficiency of the measurements.

Figure 3A:
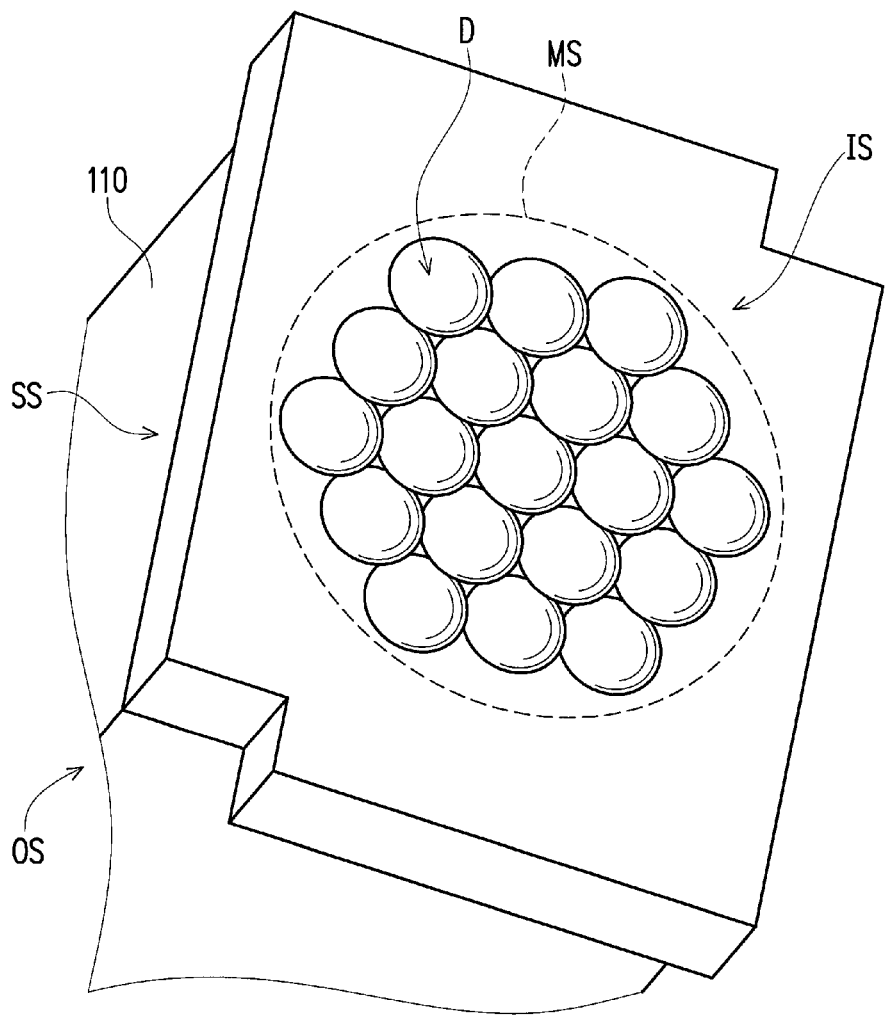
FIG. 3A illustrates a modification of a light incident surface of a lens depicted in FIG. 1A.
Figure 3B:
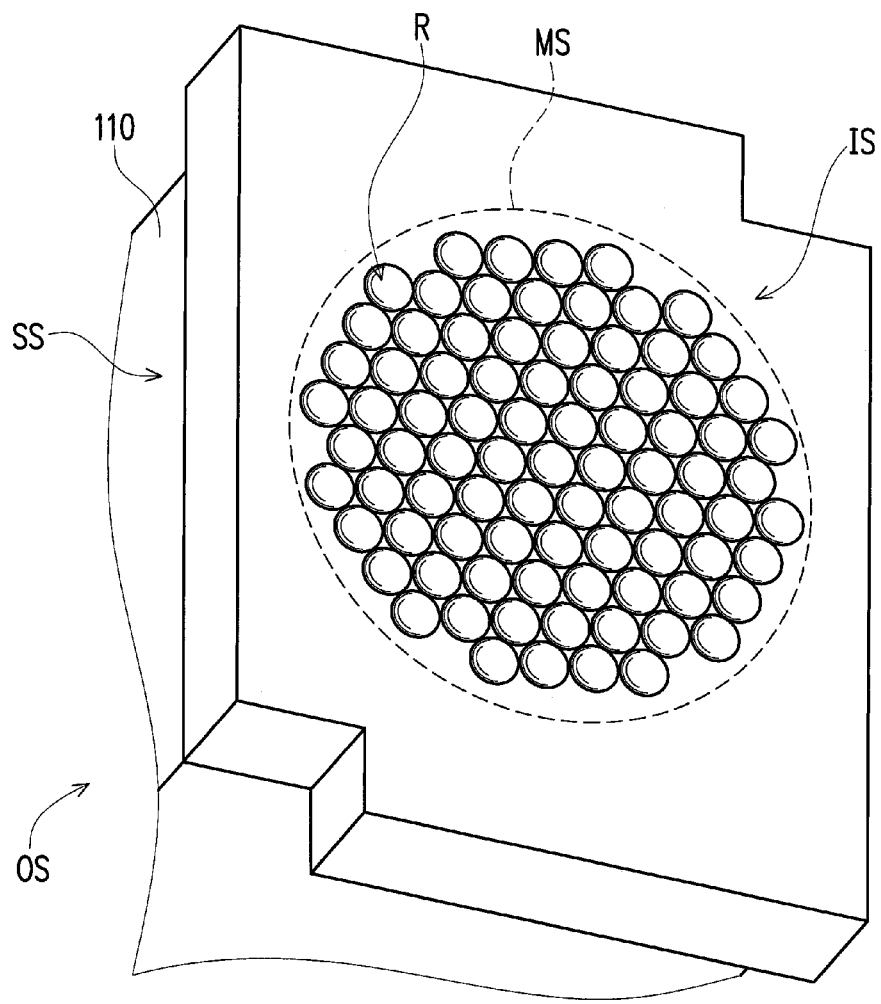
FIG. 3B illustrates another modification of a light incident surface of a lens depicted in FIG. 1A.

FIG. 3A illustrates a modification of a light incident surface of a lens depicted in FIG. 1A, and FIG. 3B illustrates another modification of a light incident surface of a lens depicted in FIG. 1A. Referring to FIG. 1A through FIG. 3B, in the embodiment, the lens 110 may have a light incident surface IS, a light emitting surface OS opposite to the light incident surface IS and a plurality of side surfaces SS connected to the light incident surface IS and the light emitting surface OS. The light beam L emitted from the light emitting unit 100 passes through the light incident surface IS and the light emitting surface OS sequentially, and the orthogonal projections PJ of the side surfaces SS on the stage P respectively form a plurality of sides of the orthogonal projections PJ of the polygon (such as the four sides of the orthogonal projection PJ of the square in FIG. 1A). In the embodiment, the light incident surface IS may be a flat surface, and the light emitting surface OS is a curved surface protruded away from the light incident surface IS. Generally speaking, the optical signal generated from the sample BS being irradiated is very weak. In the embodiment, under the circumstance that the light emitting units 100, the lenses 110 and the samples BS are maintained at an appropriate distance, the light beams L passing through the lenses 110 may be collected on the samples BS by the light emitting surfaces OS (that is, appearing to be a protruded curved surface), thereby improving the quality of measuring the properties of the samples BS. On the other hand, the lenses 110 may collect the light beams L on the samples BS to enhance the light intensity on the samples BS, and therefore, the optical measuring apparatus 10 of the embodiment is still capable of obtaining fine optical signals under the circumstance that the total energy of the light beams L emitted from the light emitting units 100 is decreased. In other words, the power consumption of the light emitting units 100 may be decreased through the optical effect of the lenses 110, and the operating temperature of the light emitting units 100 may also be decreased. In this way, the lifetime of the light emitting units 100 is extended, thereby improving the durability of the optical measuring apparatus 10.

More specifically, the lens 110 may further have a plurality of optical micro structures MS that are disposed on the light incident surface IS. As shown in FIG. 3A, the optical micro structures MS may be a plurality of recesses D dented towards the light emitting surface OS where the recesses D may be partial spherical surfaces. However, the type of the optical micro structures MS is not limited to FIG. 3A. For example, as shown in FIG. 3B, the optical micro structures MS may be a plurality of bumps R protruded away from the light emitting surface OS where the bumps R may be partial spherical surfaces. The light beams L may pass through the optical micro structures MS on the light incident surface IS when entering the lenses 110, and the light beams L are then refracted and scattered by the optical micro structures MS, such that the light beams L are further uniformly projected on the samples BS, thereby preventing the light from being overly focused on a small area of the sample BS, which may cause situations where the samples BS are damaged or decomposed. In addition, the size, shape and density of the optical micro structures MS in FIG. 3A and FIG. 3B are only illustrated for the description of the embodiments. The size, shape and density of the optical micro structures MS may both be adjusted in accordance with the actual design requirements. It should be noted that, each of the lenses 110 may have the same or different optical micro structures MS. In some embodiments, a portion of the lenses 110 may also have the same optical micro structures MS. In some other embodiments, a portion of the lenses 110 may have the optical micro structures MS and the other portion of the lenses 110 do not have the optical micro structures MS (as shown in FIG. 2A), wherein the light incident surface IS of the lens 110 without the optical micro structures MS can be, for example, a flat surface PL, or a concave surface, or a convex surface, in order to satisfy different measuring requirements. However, the invention is not limited thereto. In some embodiments, the shapes of the lenses 110 in the embodiment are identical. However, in other embodiments, different shapes of the lenses 110 may also be utilized according to the actual requirements. The shape, quantity and arrangement of the lenses 110 in the embodiment are only for illustrating the embodiment, but the invention is not limited thereto.

Moreover, each of the lenses 110 may further have two connecting portions CP opposite to each other. The two connecting portions CP are connected to the two side surfaces SS that are opposite to each other. As shown in FIGS. 1A, 2A, and 2B, the lens 110 may be fixed at the light emitting unit 100 by the two connecting portions CP. The quantity, shape and disposition location of the connecting portions CP in the embodiment are only for illustrating the embodiment, but the invention is not limited to the quantity, shape and disposition location of the connecting portions CP, which may all be designed differently according to the actual design requirements.

In addition, in the embodiment, the light emitting unit 100 may include a light emitting diode chip CH and a package structure BD covering the light emitting diode chip CH. The package structure BD may initially adjust the light distribution of the light beam L emitted from the light emitting diode chip CH, and then the lens 110 may adjust the light distribution again, such that the light distribution transmitted to the sample BS is more uniform, and simultaneously the interference may be reduced so as to avoid the measured results from being affected.

In further detail, the optical measuring apparatus 10 of the embodiment may selectively include a filter unit 140. The filter unit 140 is disposed on the transmission path of the light beam L, and is located between the light emitting unit 100 and the light detector 120, wherein the filter unit 140 may be a short-pass filter, a band pass filter, a long-pass filter or other filters, or else, a combination thereof. In the embodiment, the filter unit 140 may be disposed on the light detector 120. The filter unit 140 may effectively prevent the ambient light from outside to enter into the light detector 120, thereby improving the accuracy of the optical measuring apparatus 10 for measuring the properties of the sample BS.

The optical measuring apparatus 10 of the embodiment may further include a temperature control unit 150. The temperature control unit 150 is configured to maintain the sample BS within a predetermined temperature range, so that the properties of the sample BS measured by the optical measuring apparatus 10 may be more accurate. As shown in FIG. 1A, in the embodiment, the temperature control unit 150 may be disposed beside each of the accommodating spaces MF on the stage P. However, in other embodiments, the temperature control unit 150 may also be an air-conditioning system, or may be disposed on other locations of the optical measuring apparatus 10 in order to control the temperature of the samples BS.

Figure 4:
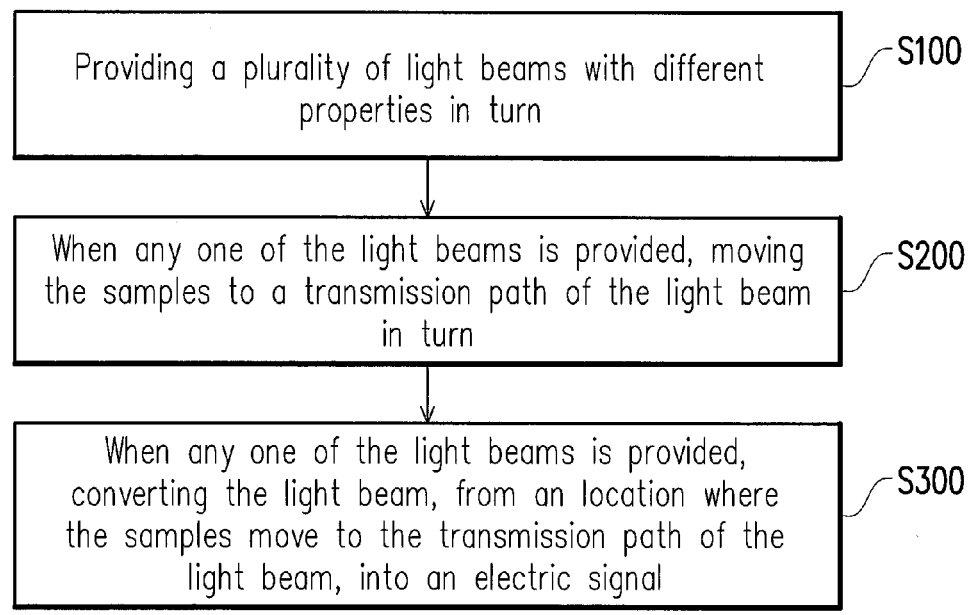
FIG. 4 is a flowchart of an optical measuring method according to another embodiment of the invention.

FIG. 4 is a flowchart of an optical measuring method according to another embodiment of the invention, wherein the apparatus for implementing the optical measuring method may be referred to the optical measuring apparatus of the embodiment in FIG. 1A, but the embodiment is not limited thereto. Referring to FIG. 1A and FIG. 4, in the embodiment, the optical measuring method is adapted to measure a plurality of samples BS, and the optical measuring method includes: providing a plurality of light beams L with different properties in turn (step S100); when any one of the light beams L is provided, moving the samples to a transmission path of the light beam L in turn (step S200); and when any one of the light beams L is provided, converting the light beam L, from a location where the samples BS move to the transmission path of the light beam L, into an electric signal ES (step S300). Since the light beams L with different properties are provided in turn, the samples BS may be avoided from being irradiated simultaneously by the light beams L with different properties, and thus the interference may not be generated to affect the measured results, as shown in the embodiment of FIG. 1A. Any one of the light beams L is capable of irradiating the samples BS in turn, and the generated electric signal ES is the electric signal ES converted by the light detector 120. Subsequently, another light beams L may be turned on so as to provide another light source with another property. In the embodiment, step S200 through step S300 may be implemented repeatedly until the light emitting units 100 have all emitted the light beams L to measure the properties of the samples BS. In this way, the samples BS and a plurality of optical signals from each of the samples BS may be accurately measured without interference between the light beams L of different optical properties, significantly improving the reliability and efficiency of the measurements. The apparatus related to the optical measuring method referred to in the embodiment is illustrated in FIG. 1A through FIG. 3B. It should be noted that each of the light beam L may be provided in turn in the embodiment. It should also be noted that the lens 110 in other shapes, such as cylindrical, besides the illustrated shape in the embodiment of FIG. 2A, may also achieve the desired measurement reliability and efficiency.

In one embodiment, the method for providing the plurality of light beams L with different properties in turn may comprise the following process. One of the light beams L is firstly provided to be the measuring light source and after all the samples BS on the stage P are irradiated and the respective optical signals thereof are detected (such as the stage P has rotated one or more laps), another light beam L is then provided to be the measuring light source and all the samples BS on the stage P are irradiated and the respective optical signals thereof are detected. Similarly, the aforementioned procedure continues until all the samples BS are respectively irradiated by all the light beams L with different properties in the light emitting unit and the optical signals thereof are all detected. All the samples BS on the stage P are irradiated and the respective optical signals thereof are detected. In other words, the light beams L with different properties being provided in turn as the measuring light sources may be cycled in turn once or more than once. In yet another embodiment, the light beams L with different properties being provided in turn may be sequentially provided in accordance with a certain order, which can be sequentially repeated in the same order, for one or more times. For instance, the light emitting units may sequentially emit the light beams L by the order of 1001, 1002, 1003, 1004, 1005, 1006 and 1007, or the light emitting units may sequentially emit the light beams L from 1007 to 1001, or the light emitting units may sequentially emit the light beams L in the order of 1001, 1004, 1003, 1002, 1007,

1005 and 1006. And the said light emitting order of light beams L can be repeated until the signal measurement is finished.

More specifically, in the embodiment, the method for moving the samples BS to the transmission path of the light beam L in turn may include rotating the samples BS around a rotation center GC1 in order for the samples BS to move to the transmission path of the light beam L in turn. For instance, the stage P in FIG. 1A may rotate continuously to drive the samples BS to move consecutively through the transmission path of the light beam L in turn, increasing the efficiency for measuring the properties of the samples BS, wherein the samples BS may include a biological sample or a non-biological sample. Moreover, the samples BS may also be a plurality of identical samples BS or individually different samples BS, but the invention is not limited thereto.

In addition, the method for moving the samples BS to the transmission path of the light beam L in turn may be implied to move the samples BS to the transmission path of the light beam L in turn once, such as rotating the samples BS one lap when the light emitting units 100 keep emitting the light beams L. Alternatively, the method for moving the samples BS to the transmission path of the light beam L in turn may be implied to move the samples BS to the transmission path of the light beam L in turn many times, such as rotating the samples BS many laps when the light emitting units 100 keep emitting the light beams L. The method for moving the samples BS to the transmission path of the light beam L in turn may be to move the samples BS sequentially to the transmission path of the light beam L in accordance with a certain order. For instance, when the light emitting units 100 keep emitting the light beams L, the samples BS are moved sequentially in a clockwise direction to the transmission path of the light beam L, or the samples BS are moved sequentially in a counter-clockwise direction to the transmission path of the light beam L. Alternatively, when the light emitting units 100 keep emitting the light beams L, the samples BS may firstly be moved sequentially in a certain direction (such as, either clockwise or counter-clockwise direction) to the transmission path of the light beam L, and then moved sequentially in another direction (such as, either counter-clockwise or the clockwise direction, namely, the direction different from the preceding direction) to the transmission path of the light beam L. In other words, when the light emitting units 100 keep emitting the light beams L, the samples BS may be forwardly rotated (or reversely rotated) one or many laps, and then reversely rotated (or forwardly rotated) one or many laps. Alternatively, the samples BS may also be successively forwardly and reversely rotated when the light emitting units 100 keep emitting the light beams L.

In addition, the optical measuring method may further include applying a plurality of lenses 110 to limit irradiation ranges of the light beams L respectively, wherein when one of the samples BS moves to the transmission path of any one of the light beams L, another adjacent sample BS of the samples BS is located outside the irradiation range of the light beam L. For example, the light fringes ZS on the directions along the perpendicular bisector half lines SL of the four sides of the orthogonal projection PJ are not overlapped with the adjacent accommodating spaces MF, through the designed arrangement and angle of the lenses 110 as shown in FIG. 1A, such that the interference between the light beams L of different properties may be prevented, and the reliability of the measurements may further be enhanced.

In the embodiment, the optical measuring method may further include: analyzing the electric signals ES converted from the light beams L in turn, wherein when any one of the light beams L is provided, the electric signal ES converted from the light beam L is analyzed. For example, as described in the embodiment of FIG. 1A, when a single light emitting unit 1002 is driven and emits light, the light detector 120 receive the optical signals generated from the samples BS (that are irradiated by the light emitting unit 1002) and convert the optical signals into the electric signals ES. Here, the control unit 130 may analyze the electric signals ES, thereby determining the property to be measured by the corresponding light emitting unit 1002 in the samples BS. When the light emitting unit 1002 is turned off and another light emitting unit 1003 is driven to emit and repeated the similar measuring process as the light emitting unit 1002, the control unit 130 also analyzes the electric signals ES generated from the corresponding samples BS (that are irradiated by the light emitting unit 1003), thereby determining the property of the samples BS to be measured by the corresponding light emitting unit 1003. Consequently, the control unit 130 of the embodiment may sequentially obtain and analyze the properties of the samples BS corresponding to light sources with different wavelengths, so that the efficiency for analyzing the measured samples BS may further be enhanced. In addition, the optical signals of the samples BS are usually relatively weak, therefore, the optical measuring method in the embodiment may also include: amplifying the electric signals ES converted respectively from the light beams L; and analyzing the amplified electric signals ES so as to determine the properties of the samples BS respectively.

In summary, the optical measuring apparatus in an embodiment of the invention may vary the illuminating range and shape of the light emitting units through the lenses disposed on the light emitting units, so as to reduce the interferences between the lights of the light emitting units on the samples located at the accommodating spaces on the stage. The optical measuring apparatus in another embodiment of the invention may sequentially turn on the plurality of light emitting units with different properties (such as different wavelength ranges) and detect the different properties of the plurality of samples in turn, through moving the accommodating spaces to the transmission paths of the light beams (with different properties) emitted from the light emitting units with different properties in turn. Such optical measuring apparatus may reduce the interferences from the light sources through collocating with the lens arrangement when more than one light beams of different properties of the light emitting unit are simultaneously turned on so as to detect the different properties of the plurality of samples at the same time. In addition, the optical measuring method in another embodiment of the invention may measure the properties of the samples and reduce the interferences between the light beams with different properties, through providing the plurality of light beams with different properties in turn and moving the samples to the transmission path of the light beam in turn when any one of the light beams is provided.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An optical measuring apparatus adapted to measure at least one sample, the optical measuring apparatus comprising:

at least one light emitting unit, configured to emit a light beam;

a stage, disposed on a transmission path of the light beam, and comprising a plurality of accommodating spaces, wherein the accommodating spaces accommodate the sample respectively, and the accommodating spaces move to the transmission path of the light beam in turn;

at least one lens, disposed on the transmission path of the light beam and located between the light emitting unit and the stage, and an orthogonal projection of the lens on the stage appearing to be a polygon, wherein when one of the accommodating spaces moves to the transmission path of the light beam, a perpendicular bisector half line of each side of the polygon is not overlapped with another adjacent accommodating space of the accommodating spaces, wherein the perpendicular bisector half line is taken a midpoint of the side of the polygon as a starting point, and is the line extending along the perpendicular bisector half line of the side away from the polygon; and at least one light detector, disposed on the transmission path of the light beam from the stage, so as to detect the light beam.

2. The optical measuring apparatus as claimed in claim 1, wherein the sample comprises a biological sample or a non-biological sample.

3. The optical measuring apparatus as claimed in claim 1, wherein the at least one lens comprises a plurality of lenses, the at least one light emitting unit comprises a plurality of light emitting units and the at least one light detector comprises a plurality of light detectors, wherein the light beams emitted from the light emitting units are respectively transmitted to the stage through the lenses and are respectively transmitted to the light detectors, and the stage is rotated in order for the accommodating spaces to move to the transmission paths of the light beams in turn, wherein the light beams emitted from the light emitting units are respectively a plurality of light beams with different properties.

4. The optical measuring apparatus as claimed in claim 3, further comprising:
a control unit, electrically connected to the light emitting units and the light detectors, the control unit driving the light emitting units to emit the light beams in turn, wherein when any one of the light emitting units emits one of the light beams, the accommodating spaces move to the transmission path of the light beam in turn, the light detectors convert the measured light beams into a plurality of electric signals for transmitting to the control unit, and the control unit analyzes the electric signals.

5. The optical measuring apparatus as claimed in claim 4, further comprising:
an actuator, connected to the stage so as to drive the stage to rotate, wherein the control unit is electrically connected to the actuator and causes light-emitting times of the light emitting units and the rotating time of the stage to cooperate with each other.

6. The optical measuring apparatus as claimed in claim 3, further comprising:
a control unit, electrically connected to the light emitting units and the light detectors, and the control unit driving the light emitting units to emit the light beams at the same time, wherein the accommodating spaces move to the transmission paths of the light beams in turn, the light detectors convert the measured light beams into a plurality of electric signals for transmitting to the control unit, and the control unit analyzes the electric signals.

7. The optical measuring apparatus as claimed in claim 3, wherein the stage rotates continuously when the light detector detects the light beam.

8. The optical measuring apparatus as claimed in claim 3, wherein wavelength ranges of the light beams are different from each other.

9. The optical measuring apparatus as claimed in claim 3, wherein the lens has a light incident surface, a light emitting surface opposite to the light incident surface and a plurality of side surfaces connected to the light incident surface and the light emitting surface, wherein the light beam emitted from the light emitting unit passes through the light incident surface and the light emitting surface sequentially, and the orthogonal projections of the side surfaces form the plurality of sides of the respective polygon on the stage.

10. The optical measuring apparatus as claimed in claim 9, wherein the light incident surface is a flat surface and the light emitting surface is a curved surface protruded away from the light incident surface.

11. The optical measuring apparatus as claimed in claim 9, wherein the light incident surface is a curved surface protruded towards the light emitting unit, and the light emitting surface is a curved surface protruded away from the light incident surface.

12. The optical measuring apparatus as claimed in claim 9, wherein the at least one lens comprises a plurality of lenses, wherein each of the light incident surfaces of at least a portion of the lenses has a plurality of optical micro structures, and the optical micro structures belonging to the different lenses are identical to each other or at least partially different from each other.

13. The optical measuring apparatus as claimed in claim 1, further comprising:
a filter unit, disposed on the transmission path of the light beam and located between the light emitting unit and the light detector.

14. The optical measuring apparatus as claimed in claim 1, further comprising:
a temperature control unit, maintaining a temperature of the sample within a predetermined temperature range.

15. An optical measuring apparatus adapted to measure at least one sample, the optical measuring apparatus comprising:
a plurality of light emitting units, emitting a plurality of light beams with different properties in turn;
a stage, disposed on transmission paths of the light beams, and comprising a plurality of accommodating spaces, wherein the accommodating spaces accommodate the sample respectively, wherein when any one of the light emitting units emits one of the light beams, the accommodating spaces move to the transmission path of the light beam in turn;
a plurality of lenses, respectively disposed on the transmission paths of the light beams and disposed between the light emitting units and the stage, wherein each of the lenses has a light incident surface, a light emitting surface opposite to the light incident surface and a plurality of side surfaces connected to the light incident surface and the light emitting surface, and the light beam emitted from each of the light emitting units passes through the light incident surface and the light emitting surface sequentially, and an orthogonal projection of each of the lenses on the stage appears to be a polygon, and the orthogonal projections of the side surfaces of the lens on the stage form the sides of the polygon, wherein a perpendicular bisector half line of each side of the polygon is not overlapped with another adjacent accommodating space of the accommodating spaces, wherein the perpendicular bisector half line is taken a midpoint of the side of the polygon as a starting point, and is the line extending along the perpendicular bisector half line of the side away from the polygon;

a plurality of light detectors, respectively disposed on the transmission paths of the light beams from the stage so as to detect the respective light beams; and a control unit, electrically connected to the light emitting units and configured to drive the light emitting units to emit the light beams with different properties in turn.

16. The optical measuring apparatus as claimed in claim 15, wherein the sample comprises a biologic sample or a non-biologic sample.

17. The optical measuring apparatus as claimed in claim 15, wherein each of the light incident surfaces of at least a portion of the lenses has a plurality of optical micro structures, and the optical micro structures belonging to the different lenses are identical to each other or at least partially different from each other.

18. The optical measuring apparatus as claimed in claim 15, wherein the control unit is also electrically connected to the light detectors, and wherein when any one of the light emitting units emits one of the light beams, the accommodating spaces move to the transmission path of the light beam in turn, the light detectors convert the measured light beams into a plurality of electric signals for transmitting to the control unit, and the control unit analyzes the electric signals.

19. The optical measuring apparatus as claimed in claim 18, further comprising:

an actuator, connected to the stage so as to drive the stage to rotate, wherein the control unit is electrically connected to the actuator and causes light-emitting times of the light emitting units and a rotating time of the stage to cooperate with each other.

20. The optical measuring apparatus as claimed in claim 15, wherein the stage rotates continuously when the light detector detects the light beam.

21. The optical measuring apparatus as claimed in claim 15, wherein wavelength ranges of the light beams are different from each other.

\* \* \* \* \*